United States Patent [19]
Brakas

[11] Patent Number: 5,511,251
[45] Date of Patent: Apr. 30, 1996

[54] HEAD STRAP FOR SUNGLASSES

[76] Inventor: Yvonne J. Brakas, 12850 Opalocka Dr., Chesterland, Ohio 44026

[21] Appl. No.: 333,971

[22] Filed: Nov. 3, 1994

[51] Int. Cl.$^6$ ................................ A61F 9/02; G02C 3/00
[52] U.S. Cl. .................. 2/452; 2/450; 2/451; 351/116; 351/123; 351/156
[58] Field of Search ................. 2/452, 11, 15, 2/426, 431, 448, 449, 450, 451, 9, DIG. 11; 351/111, 116, 123, 156, 157; 24/3 C

[56] References Cited

U.S. PATENT DOCUMENTS

| | | |
|---|---|---|
| D. 294,833 | 3/1988 | Holden . |
| 4,106,119 | 8/1978 | Taupin . |
| 4,405,212 | 9/1983 | Cooper . |
| 4,564,960 | 1/1986 | Nishiyama ................... 2/452 |
| 4,621,378 | 11/1986 | Hatchman . |
| 4,657,364 | 4/1987 | Murrell ..................... 351/123 |
| 4,930,885 | 6/1990 | Laschober ................... 351/156 |
| 4,976,531 | 12/1990 | Kahaney . |
| 4,978,210 | 12/1990 | Lundbeck . |
| 5,002,381 | 3/1991 | Murrell ..................... 351/123 |
| 5,183,059 | 2/1993 | Leonardi . |
| 5,201,856 | 4/1993 | Edwards . |
| 5,386,254 | 1/1995 | Kahaney ..................... 351/116 |
| 5,406,340 | 4/1995 | Hoff ........................ 351/156 |

*Primary Examiner*—Michael A. Neas
*Attorney, Agent, or Firm*—Michael A. Catania

[57] ABSTRACT

An innovative head strap for utilization with sunglasses which provides a tight fit about the user's head allowing for a tight headset seal when the sunglasses are worn simultaneously with a headset. The head strap is composed of two members each having an elastic conformable pocket for insertion of a connection piece which connects each of the members to the pair of sunglasses. The head strap is adjustable, allowing for conformance to most users' heads. The head strap is composed of an elastic material which has a durable external surface and a cushion-like internal surface.

10 Claims, 1 Drawing Sheet

BEST AVAILABLE COPY

HEAD STRAP FOR SUNGLASSES

BACKGROUND OF THE INVENTION

1) Field of the Invention

The present invention relates generally to apparatuses for holding glasses on a user's head, and more particularly to an elastic head strap for utilization in conjunction with sunglasses.

2) Description of the Related Art

The newest innovation in eye wear are sunglasses designed of molded plastic lens which conform over, under and around the sides of an user's eyes providing a full one-hundred eighty degrees of vision without distorting or frame blockage. These all-around protection sunglasses are of great benefit to aviators who might be distracted by light entering from the sides of conventional aviator glasses. This innovated style of sunglasses is also beneficial to sports enthusiasts, from skiers to cyclists. Zurich International Corporation of Chico, Calif. manufacturers and markets such sunglasses. However, this new style of sunglasses still has rigid temples or sides which may be an irritant to the user, and which do not allow aviators to have a proper seal when using headsets along with the sunglasses. An improper headset seal would allow unwanted airplane noises and the like to be heard by the user. What is needed is a way to properly retain the sunglasses on a user's head and also allow for a proper headset seal.

The innovative minds of the eye wear industry have brought forth several inventions for retaining glasses on a user's head. Kahaney, U.S. Pat. No. 4,976,531, discloses such an invention. Kahaney discloses a retainer strap for eyeglasses which attaches to the temples of eyeglasses and seeks to retain the eyeglasses about the user's head during active moment by the user. Edwards, U.S. Pat. No. 5,201,856, also discloses an invention for retaining eyeglasses. The Edward's invention, as with the Kahaney invention, discloses a retainer which is used with eyeglasses. However, Edward's invention encompasses the temples of the eyeglasses while retaining the eyeglasses on the user's head. Although, these and other inventions retain glasses on an user's head, they won't allow for a tight seal when used in conjunction with a headset.

SUMMARY OF THE INVENTION

The present invention provides a novel substitution for the temples of the above-mentioned innovative all-around blockage sunglasses which provide one-hundred eighty degree coverage of the user's eyes. The present invention is a head strap which is substituted for the conventional temples of the sunglasses. The head strap fits snugly and comfortably on the user's head and allows for a proper headset seal when the sunglasses are used simultaneously with a headset by the user. The head strap substantially conforms to the user's head allowing for a tight, yet comfortable fit. This tight fit allows the headset to create a proper seal around the user's ears which prevents unwanted noise from entering the user's ear.

The head strap of the present invention is utilized in conjunction with a pair of sunglasses as a substitute for the conventional temples used to retain the sunglasses on the user's head. The novel head strap comprises a left member and right member with each member having a connection end and an attachment end. Each member also has an external surface and an internal surface. At the connection end of each member, there is a novel closed loop which forms an elastic conformable pocket. At the attachment end of each of the members there is an attachment means for attaching the members to each other. The left member has its attachment means located on its external surface while the right member has its attachment means located on its internal surface. The attachment means mate to each other to form a continuous strap around the user's head from one end of the sunglasses to the other end of the sunglasses.

The head strap also includes a left connection means and a right connection means. Each of the connection means are inserted into the corresponding elastic conformable pockets of the members. Each of the elastic conformable pockets securely encircles the corresponding connection means. Each of the connection means allow for connection of the head strap to the sunglasses. The left connection means is connected to the left end of the sunglasses and the right connection means is connected to the right end of the sunglasses. Each of the connection means are connected substantially perpendicular to the sunglasses In the preferred embodiment, each of the connection means are insertable pieces having an upward extending prong and a downward extending prong for connection to the sunglasses. The connection means imitate the connection apparatus of the temples of the sunglasses, and have their prongs inserted into the slots which are revealed when the temples are removed from the sunglasses. Other embodiments of the connection means would allow the connection means to be connected to traditional glasses with only substitution of the temples.

It is the primary object of the present invention to provide a head strap for retaining sunglasses on an user's head while allowing for a proper headset seal when utilized simultaneously with headsets.

It is a further object of the present invention to provide a head strap as a substitution for conventional temples of sunglasses in order to provide a more comfortable and snug fit for the user of the sunglasses.

It is a further object of the present invention to provide a releasable head strap for utilization with sunglasses having substantially one-hundred eighty degree coverage of the user's eyes.

BRIEF DESCRIPTION OF THE DRAWINGS

The present invention is further described in connection with the accompanying drawings, in which:

There is illustrated in FIG. 1 a top perspective of the head strap of the present invention coupled with a pair of sunglasses, with the members of the head strap unattached to each other.

Figure 2:
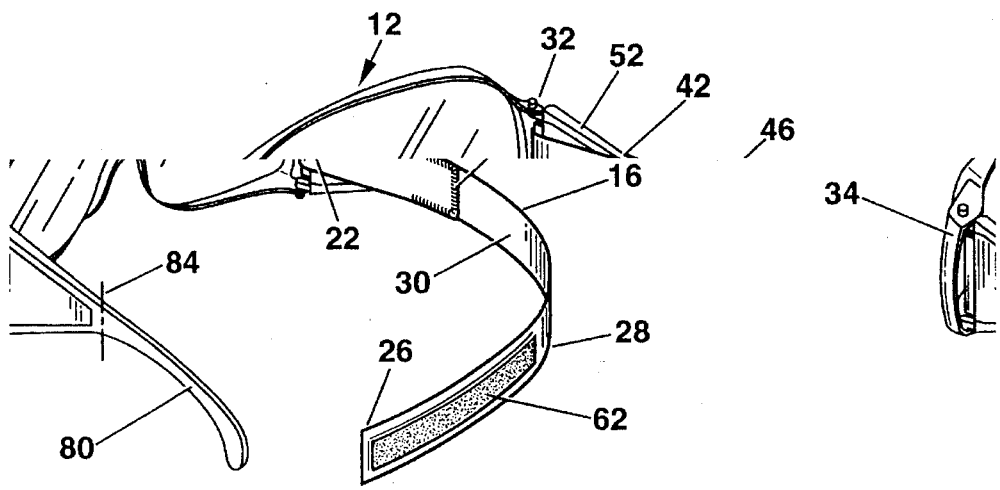

There is illustrated in FIG. 2 a top perspective of the head strap of the present invention with the right member connected to the right side of the sunglasses and the left temple of the sunglasses still connected to the left side of the sunglasses.

There is illustrated in FIG. 3 a side perspective of a connection piece of the present invention disengaged from the pocket of the head strap of the present invention.

DETAILED DESCRIPTION OF THE INVENTION

Figure 1:
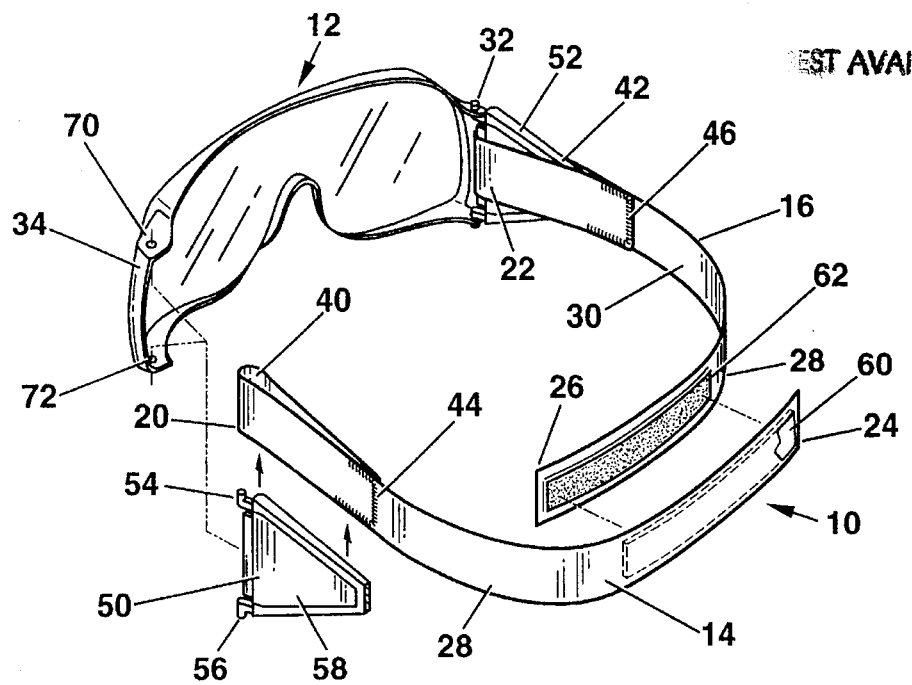

There is illustrated in FIG. 1 a top perspective of the head strap of the present invention coupled with a pair of sunglasses, with the members of the head strap unattached to each other. Referring to FIG. 1, the head strap 10 of the present invention is coupled to sunglasses 12. For illustrative purposes, sunglasses 12 are sunglasses of the all-around blockage type as disclosed in Holden, U.S. Pat. No. Des. 294,833. Head strap 10 includes left member 14 and right member 16, both members 14 and 16 have a connection end 20 and 22, and an attachment end 24 and 26. Both members 14 and 16 are connected to the sunglasses 12. Connection end 20 of left member 14 is connected to the left end 34 of sunglasses 12. Connection end 22 of right member 16 is connected to right end 32 of sunglasses 12.

Each of the members 14 and 16 have an external surface 28 and an internal surface 30. Internal surface 30 is generally facing and adjoined to the surface of the user's head. External surface 28 is generally facing away from the user's head and is exposed to the climatic elements. Therefore, the internal surface 30 is designed to create a comfortable mating with the user's head whereas the external surface is designed to withstand the climatic elements. Thus, the preferred embodiment would have internal surface 30 composed of a soft cushion-like material while the external surface 28 would be composed of a durable element-resistant material. Each of the members 14 and 16 are generally rectangular in shape and of an equal predetermined length. In the preferred embodiment, each member 14 and 16 are approximately thirty-three centimeters in length and two and one-half centimeters in width.

On the internal surface 30, at the attachment end 24 of left member 14 is the first attachment means 60. On the external surface 28 at the attachment end of right member 16 is the second attachment means 62. The first and second attachment means 60 and 62 mate with each other to form a substantially continuous head strap 10 from the right side 32 of the sunglasses 12 to the left side 34 of sunglasses 12. The attachment means 60 and 62 are such that the user can adjust the length of the head strap 10 to conform to a longer or shorter circumference by moving the member 14 and 16 toward each other along the horizontal plane or away from each other along the horizontal plane. If the user desires to have a tighter fitting head strap 10, the user will move attachment end 26 of right member 16 toward left member 14 along the horizontal plane, and simultaneously move attachment end 24 of left member 14 toward right member 16 along the horizontal plane. If the user desires to have a looser fitting head strap 10, the user will move attachment end 26 of right member 16 away from left member 14 along the horizontal plane, and simultaneously move attachment end 24 of left member 14 away from right member 16 along the horizontal plane. In the preferred embodiment, first attachment means 60 and second attachment means 62 are hook and loop fastener straps sewn to each of the members 14 and 16 with the hook and loop fastener surface of the first attachment means facing the complementary hook and loop fastener surface of the second attachment means.

At connection end 20 of left member 14 and at connection end 22 of right member 16, there are elastic conformable pocket 40 and elastic conformable pocket 42, respectively. The novel pockets 40 and 42 are created by looping the respective connection ends 20 and 22 of the members 14 and 16 back on themselves to close the loop. What was the peripheral of each of the connection ends 20 and 22, is then sewn at stitches 44 and 46 to the internal surface 30 of each of the members 14 and 16 to form the elastic conformable pockets 40 and 42. The novel pockets 40 and 42 securely constrain a left connection piece 50 and a right connection piece 52, respectively. These connection pieces 50 and 52 are inserted into the corresponding pockets 40 and 42 thereby providing a connection means for head strap 10 to connect to sunglasses 12. In the preferred embodiment, the novel pockets 40 and 42 are each created by looping approximately five centimeters of the connection ends 20 and 22 back on themselves to close the loop.

There is illustrated in FIG. 2 a top perspective of the head strap of the present invention with the right member connected to the right side of the sunglasses and the left temple of the sunglasses still connected to the left side of the sunglasses. There is illustrated in FIG. 3 a side perspective of a connection piece of the present invention disengaged from the pocket of the head strap of the present invention. Referring to FIGS. 2 and 3, the connection means are connection pieces 50 and 52 which are exemplified in FIG. 3 as connection piece 50. In the preferred embodiment, the connection pieces 50 and 52 each have a flat body 58, an upward extending prong 54 and a downward extending prong 56. In the preferred embodiment, the connection pieces 50 and 52 are designed to couple with slots 70, 72, 74 and 76 of sunglasses 12, slots 74 and 76 not shown. The slots 70, 72, 74 and 76 are exposed when the conventional temples 80 and 82, temple 82 not shown, for the left side and right side of sunglasses 12 are removed and substituted with head strap 10 for retaining sunglasses 12 on the user's head. In the preferred embodiment, all-around protection sung)asses as claimed in Holden, U.S. Pat. No. Des. 294,833, are utilized in conjunction with head strap 10. However, the head strap 10 of the present invention may be utilized with safety glasses, night vision glasses, and the like. The temples 80 and 82 are removed from the Holden sunglasses to create sunglasses 12 which have slots 70, 72, 74 and 76 exposed and ready for coupling with connection pieces 50 and 52. Upward extending prong 54 and downward extending prong 56 of each connection piece 50 and 52 are engaged with slots 70, 72, 74 and 76 of sunglasses 12 to connect head strap 10 to sunglasses 12.

While the preferred embodiment of the invention has been shown and described, it will be apparent to those skilled in this art that various modifications may be made in the embodiment without departing from the spirit of the present invention.

Therefore, the embodiments of the invention in which an exclusive property or privilege is claimed are defined as follows:

1. A head strap for utilization with a pair of glasses, the head strap comprising:

a left member and a right member, each of said members having a connection end and an attachment end, each of said members having an external surface and an internal surface, each of said members composed of an elastic material which allows for a substantial conformance of said members to the user's head, each of said members having a closed loop at the connection end which forms an elastic conformable pocket, said left member having a first attachment means located on said internal surface at said attachment end and said right member having a second attachment means located on said external surface at said attachment end, said first attachment means mating with said second attachment means thereby forming a continuous strap around the user's head from one end of the glasses to the other end of the glasses; and, a left connection means and a right connection means, each of said connection means for connecting each of said members to the glasses, said left connection means corresponding to said left member and said right connection means corresponding to said right member, each of said connection means placed within and secured by said elastic conformable pocket of each of said members, wherein said left connection means and said right connection means are internal pieces, each of said insertable pieces having a flat central body insertable into said elastic conformable pocket of each of said members, each of said insertable pieces having an upward extending prong and a downward extending prong, each of said upward extending prongs and downward extending prongs releasably coupling with the glasses.

2. An elastic head strap for utilization in conjunction with a pair of side protection sunglasses, the sunglasses having temples which are removed, revealing two sets of apertures on each side of the frame of the sunglasses, the elastic head strap comprising:

a left member and a right member, each of said members having a connection end and an attachment end, each of said members having an external surface and an internal surface, each of said members composed of an elastic material which allows for substantial conformance of said members to the user's head, each of said members having a closed loop at said connection end which forms an elastic conformable pocket, said left member having a first attachment means located on said internal surface at said attachment end and said right member having a second attachment means located on said external surface at said attachment end, said first attachment means mating with said second attachment means thereby forming a continuous strap around the user's head from one end of the sunglasses to the other end of the sunglasses; and, a left connection piece and a right connection piece, each of said connection pieces for connecting each of said members to the sunglasses, each of said connection pieces having a flat central body insertable into said elastic conformable pocket of each of said members, each of said connection pieces having an upward extending prong and a downward extending prong, each of said upward extending prongs and downward extending prongs releasably coupling with the sunglasses.

3. The elastic head strap according to claim 2 wherein each of said members substantially conforms to user's head so as to allow for a tight headset seal when the user of said head strap simultaneously wears a headset with said elastic head strap and sunglasses.

4. The elastic head strap according to claim 2 wherein said left member and said right member are composed of an elastic cloth-like material capable of comfortably conforming to an user's head.

5. The elastic head strap according to claim 2 wherein said left member and said right member are substantially rectangular in shape, with a rectangular width essentially corresponding to the width of the frame of the glasses.

6. The elastic head strap according to claim 2 wherein said first attachment means and said second attachment means are hook and loop fastener straps sewn to said members.

7. An elastic head strap for utilization in conjunction with a pair of all-around protection sunglasses while the user of the sunglasses is simultaneously wearing a headset, the sunglasses having temples which are removed, revealing two sets of apertures on each side of the frame of the sunglasses, the elastic head strap comprising:

a left member and a right member, each of said members having a connection end and an attachment end, each of said members having an external surface and an internal surface, each of said members composed of an elastic material which allows for substantial conformance of said members to the user's head, each of said members having a closed loop at said connection end which forms an elastic conformable pocket, said left member having a first attachment means located on said internal surface at said attachment end and said right member having a second attachment means located on said external surface at said attachment end, said first attachment means mating with said second attachment means thereby forming a continuous strap around the user's head from one end of the sunglasses to the other end of the sunglasses, the head strap fitting tightly around the user's head so as to allow the headset to form a tight seal around the user's ears; and, a left connection piece and a right connection piece, each of said connection pieces for connecting each of said members to the sunglasses, each of said connection pieces having a flat central body internal into said elastic conformable pocket of each of said members, each of said connection pieces having an upward extending prong and a downward extending prong, each of said upward extending prongs and downward extending prongs releasably coupling with the sunglasses.

8. The elastic head strap according to claim 7 wherein left member and said right member are composed of an elastic cloth-like material capable of comfortably conforming to an user's head, said internal surface of each of said members composed of cushion-like material and said external surface of each of said members composed of a durable weather-resistant material.

9. The elastic head strap according to claim 7 wherein said left member and said right member are substantially rectangular in shape, with a rectangular width essentially corresponding to the width of the frame of the glasses.

10. The elastic head strap according to claim 7 wherein said first attachment means and said second attachment means are hook and loop fastener straps sewn to said members.

* * * * *